United States Patent [19]

Mumme

[11] Patent Number: 5,411,505
[45] Date of Patent: May 2, 1995

[54] SAGITTAL SAW JIG FOR FEMORAL KNEE REVISION PROSTHESIS

[75] Inventor: Charles W. Mumme, Austin, Tex.

[73] Assignee: Intermedics Orthopedics, Inc., Austin, Tex.

[21] Appl. No.: 253,102

[22] Filed: Jun. 2, 1994

[51] Int. Cl.6 .............................................. A61B 17/15
[52] U.S. Cl. ................................................... 606/88
[58] Field of Search .................................. 606/87, 88

[56] References Cited

U.S. PATENT DOCUMENTS

| | | | |
|---|---|---|---|
| 4,457,307 | 7/1984 | Stillwell | 606/88 |
| 4,722,330 | 2/1988 | Russell et al. | 606/88 |

Primary Examiner—Tamara L. Graysay
Attorney, Agent, or Firm—John R. Merkling

[57] ABSTRACT

A jig for resecting the distal end of a femur to receive a femoral component of a knee prosthesis. The jig has independent medial and lateral condyle sagittal saw guides. The guides aid a surgeon in cutting three of four resected surfaces or planes for each condyle. The femoral component accepts shims over either condyle to compensate for uneven loss of healthy bone. The shims do not change the internal geometry of the femoral component, but associate each proximal displacement with an anterior displacement of the geometry. Each saw guide slides on a slanted dovetail track so that the proper amount of anterior displacement can be maintained so that shims may maintain the common internal geometry.

16 Claims, 4 Drawing Sheets

SAGITTAL SAW JIG FOR FEMORAL KNEE REVISION PROSTHESIS

FIELD OF MY INVENTION

My invention relates to orthopedic surgical instruments generally and specifically to sagittal saw jigs for preparing the distal femur to receive a revision prosthesis.

BACKGROUND OF MY INVENTION

Orthopedics implants for the human knee generally have a femoral and tibial component. The tibial component is usually placed on the resected proximal surface of the tibia and frequently has a metal baseplate with a shaft extending into the medullar canal. The baseplate usually carries an ultra high molecular weight polyethylene (UHMWPE) articulating surface. The articulating surface has a medial and lateral condyle compartment. A femoral component is implanted on a resected distal end of the femur and presents artificial condyles to articulate with the condyle compartments of the tibial component. A femoral component generally comprises the condyle articulating surfaces and fixation means which may include an elongated stem which extends into the medullar canal of the patient. Such prosthesis are well-known and examples can be found in U.S. Pat. Nos. 4,963,152; 5,062,852; and 5,071,438.

For patients who require an artificial knee prosthesis, degeneration of the bone at either the tibia or femur or both may be occurring. Moreover, this degeneration may be proceeding unevenly with respect to the two condyles. It is known that some patients require a reoperation and the installation of what is called a "revision" knee prosthesis. The revision knee prosthesis is generally more massive than a so-called "primary" knee prosthesis. The revision femoral knee condylar parts may be thicker and more robust and the medullary shaft may be substantially longer. Moreover, in many cases degeneration of one condyle may be substantially more advanced than the other.

In such cases, it is advantageous to be able to retain as much bone in each condyle as possible. This, however, may result in uneven resection of the condyles. One can compensate for this disparity by providing shims which can be stacked on one condyle to raise the surfaces in an appropriate fashion.

SUMMARY OF MY INVENTION

In a knee prosthesis manufactured by my Assignee Intermedics Orthopedics, Inc., the femoral prosthesis has an internal geometry adjacent the femur which has four intersecting planes which extend from the medial side of the knee to the lateral side. Using this geometry, shims of varying thickness can be added which retain the same internal box geometry. The shims must be translated slightly anteriorly as they increase in thickness. Since the shims may be added to either condyle independently, there exists a need for an instrument to aid the surgeon in accurately cutting both condyles.

I have invented a jig with independent medial and lateral condyle sagittal saw guides. The guides aid the surgeon in cutting three of the four planes for each condyle. Each saw guide slides on a slanted dovetail track to give the proper amount of anterior displacement when shims are added, thus maintaining the common internal geometry.

With the foregoing in mind, it is the principal object of my invention to provide a sagittal saw jig for a revision knee prosthesis which has independent saw guides for each condyle.

It is a further object of my invention to provide such a jig which will maintain a common internal box geometry for installation of a knee prosthesis with shims.

These and other objects and features of my invention will be apparent from the following detail description taken with respect to the accompanying drawings.

DETAILED DESCRIPTION OF MY PREFERRED EMBODIMENT

Figure 1:
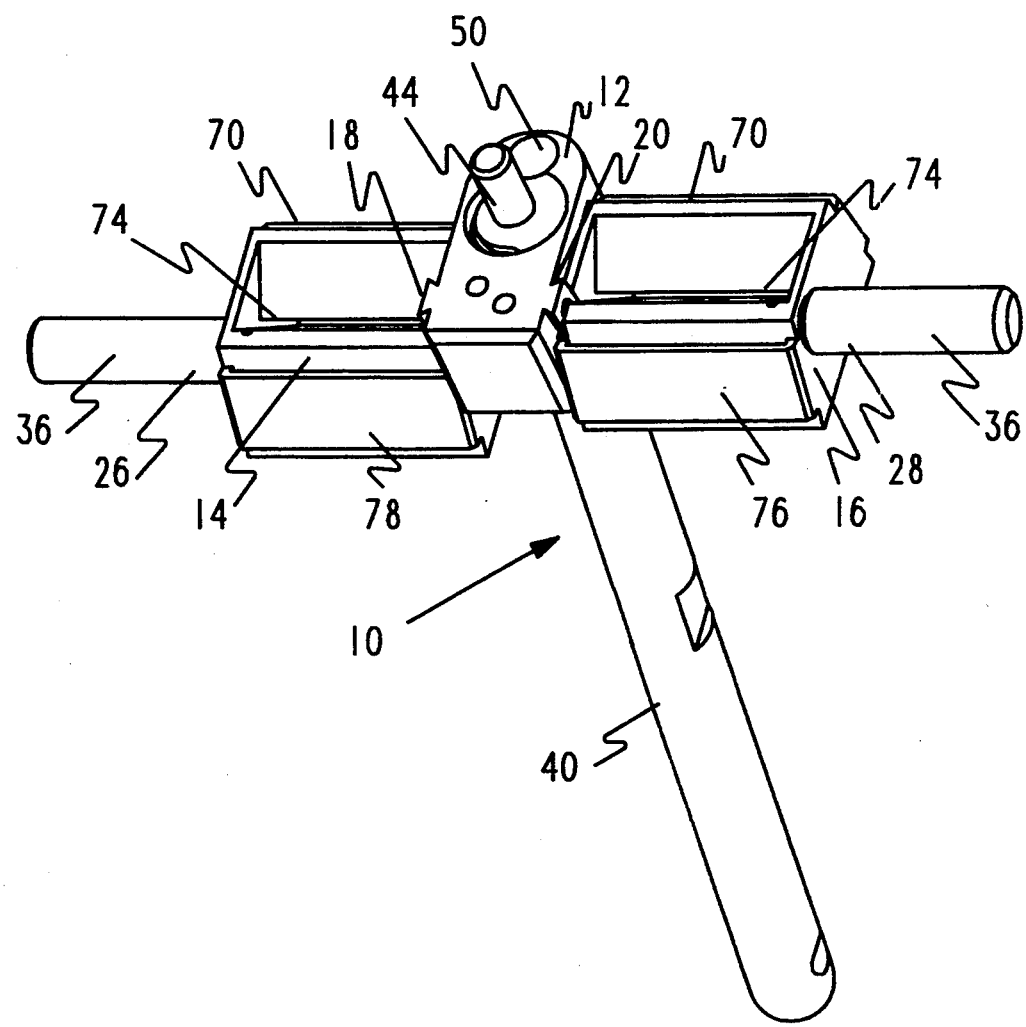
FIG. 1 is a perspective view of a sagittal saw jig for a femoral knee prosthesis according to my invention.
Figure 2:
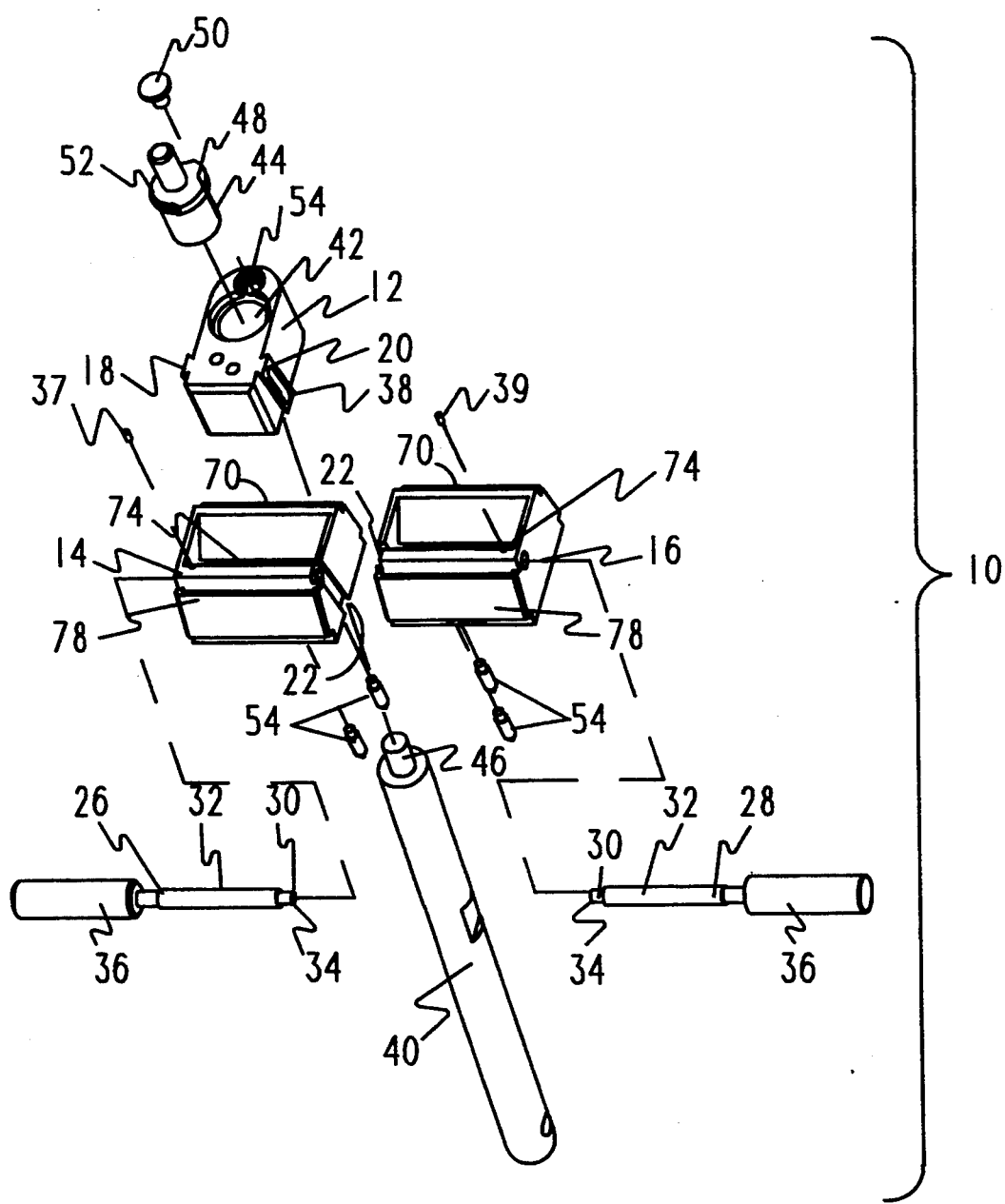
FIG. 2 is an exploded perspective view of the jig of FIG. 1.
Figure 8:
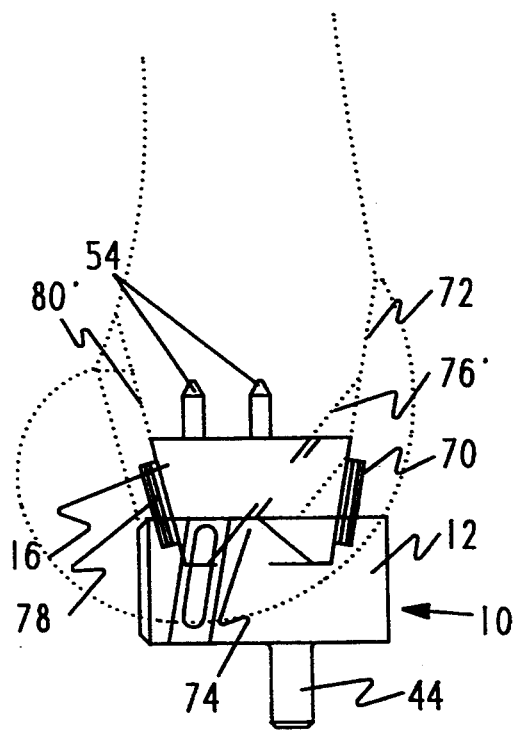
FIG. 8 is a second side plan view of selected components of the jig of FIG. 5 with the trial prosthesis shown in dotted outline.

A jig 10 for a femoral component of a prosthetic knee is shown in perspective view in FIG. 1. An exploded perspective view is shown in FIG. 2. The jig 10 according to my invention comprises a central body 12 with first and second condyle saw guides 14, 16 respectively. The central body 12 has slanted dovetails 18, 20 on opposite sides of the body 12. The dovetails are received in grooves 22, 24 on the saw guides 14, 16. As can be seen in FIG. 8, the dovetails slant with respect to the body 12, slanting slightly anteriorly as the dovetail approaches the distal end of the femur.

The saw guides 14, 16 are held in position along the length of their respective dovetail by bolts 26, 28. The bolts 26, 28 have a shank 30 which is threaded 32 in its mid section. A tip 34 is not threaded. A handle 36 is provided on each bolt so that it can be tightened or loosened without the need of an additional tool. Tightening the bolts 26, 28 forces the unthreaded tip 30 into a groove 38 in the dovetail. This pulls the saw guides 14, 16 against their dovetail and locks them in the selected position along the dovetail. The bolts 26, 28 may be trapped in the saw guides 14, 16 with set screws 37, 39 or pins. This prevents the bolts from being removed from the saw guides.

Figure 3:
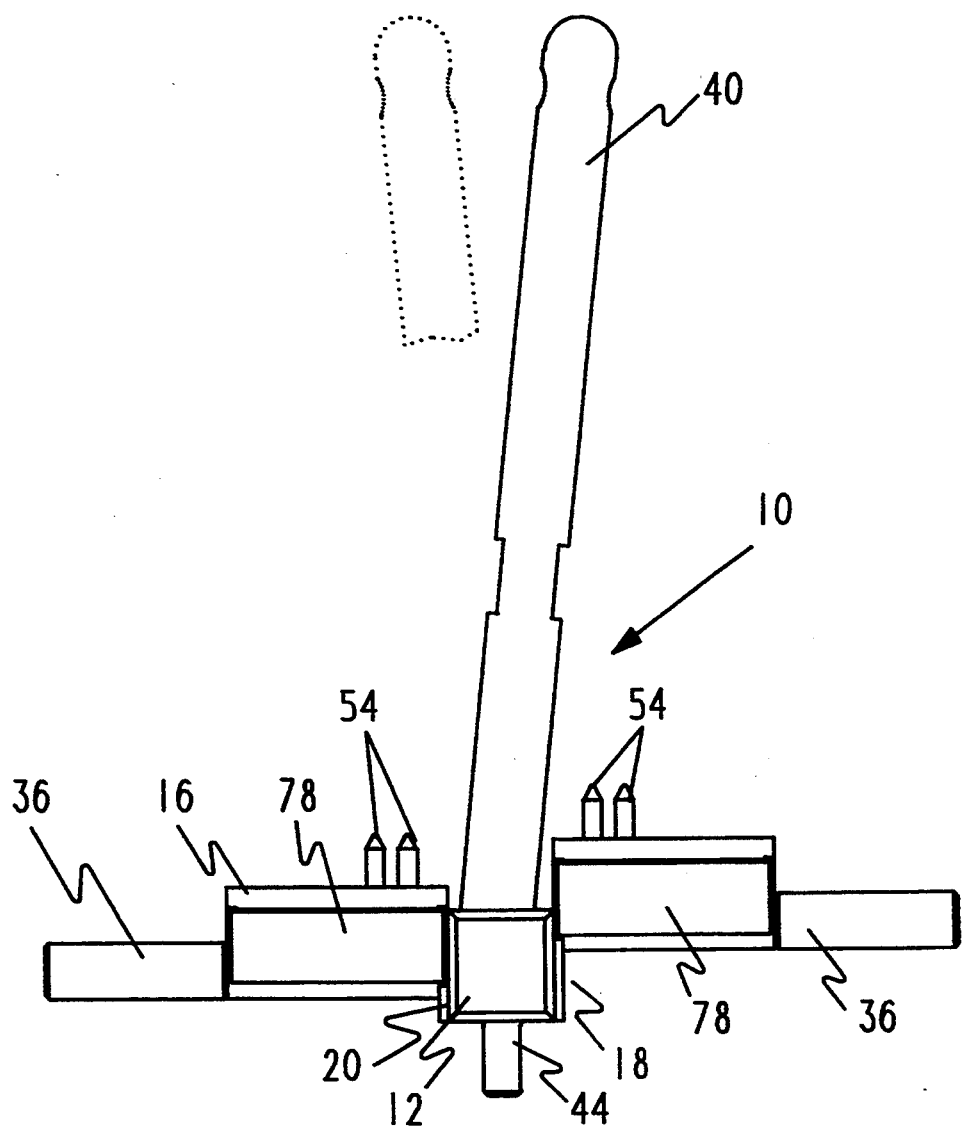
FIG. 3 is a front plan view of the jig of FIG. 1.
Figure 4:
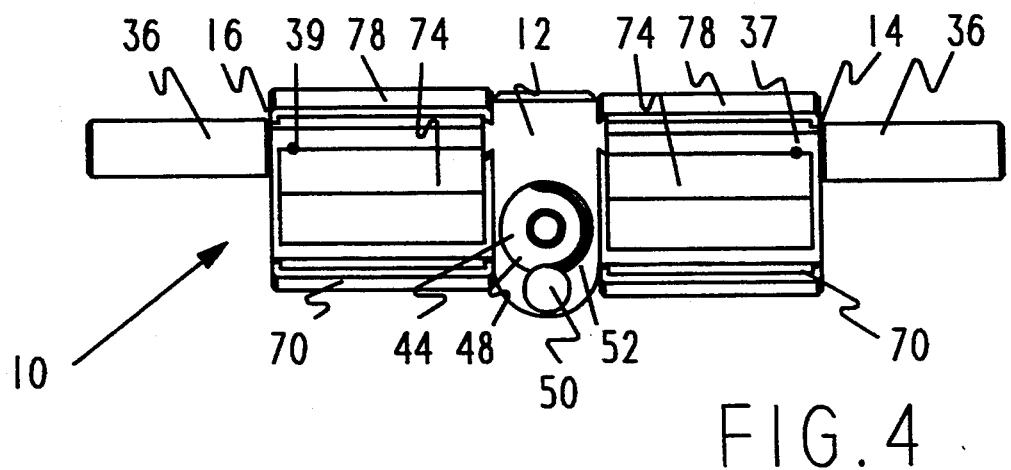
FIG. 4 is a bottom plan view of the jig of FIG. 1.
Figure 5:
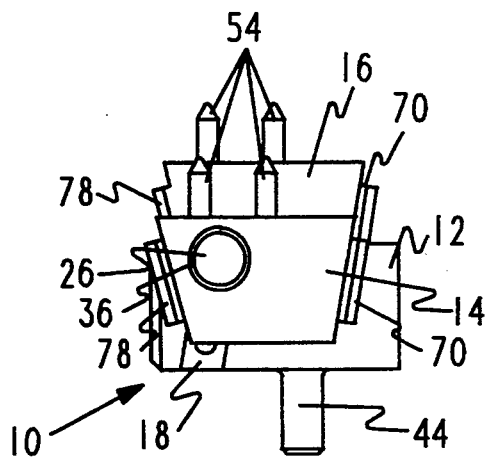
FIG. 5 is a side plan view of the jig of FIG. 1.

The jig 10 is held temporarily on the end of the femur by a trial medullar stem 40 which is adapted to extend into a bore prepared into the medullar canal of the femur. Jigs for preparing such bores are known and one such jig has been distributed by Intermedics Orthopedics, Inc. in connection with the Natural-Knee ® System, a prosthetic knee and instrumentation. As is known from anatomy, the axis of the femur and the plane of the articulating surfaces of the knee do not meet at a right angle. Consequently, the trial stem 40 should also meet the jig at less than a 90° angle as can be seen in FIG. 3. This angle could be made permanent and a separate jig provided for the right and left knee. I have also provided, however, an apparatus for reversing the inclination of the stem 40 so that the jig may be used on either the right or left knee. This apparatus comprises a through bore 42 in the central body 12 into which is fitted a cylindrical bushing 44. A pin 46 on the shaft 40 is inserted into a blind bore in the bushing 44 and is secured in any suitable conventional manner. A flange 48 on the bushing 44 interacts with a pin 50 to provide two positions for the shaft separated by 180°. The flange 48 has a relieved portion 52 which engages the pin 50. The pin 50 is press fit in a bore 55 in the body 12 to retain the cylindrical bushing 44. The bushing 44 can be rotated into position and locked there by tightening the trial stem 40 though the central block 12 and into the bushing 44. The shaft or trial stem 40 may be removed to allow the bushing 44 to be rotated 180°, then reinserted as described above, to change its angle with respect to the jig as shown in FIG. 3.

For additional stability, pins 54 can be provided as desired on each of the saw guides 14, 16.

Figure 6:
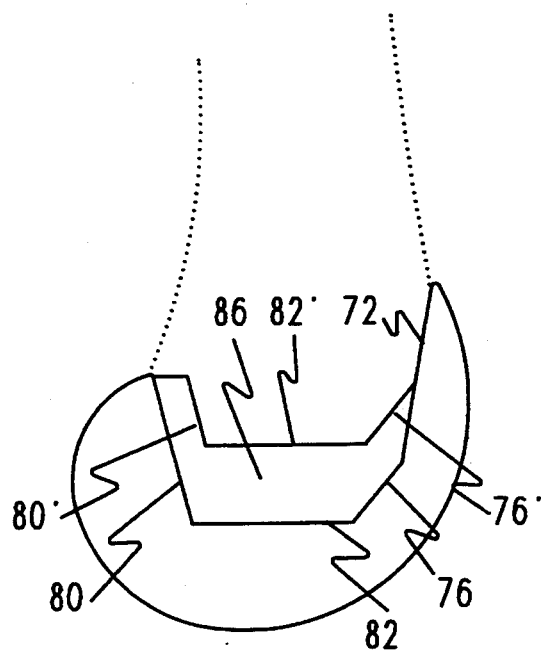
FIG. 6 is a side plan view of a femoral knee prosthesis trial implant, with a shim on one of the condyles.

I will now describe the features of the saw guides which permit guiding of a sagittal saw. Each saw guide 14, 16 provides for two anterior oblique resections and one posterior resection. A first anterior slot 70 guides the sagittal saw to make a surface for a first anterior surface 72 on a prosthesis as seen in the trial prosthesis in FIG. 6. Sawing through a second anterior slot 74 produces a second anterior surface 76 seen in FIG. 6. Finally, sawing through a posterior slot 78 produces a posterior oblique surface 80.

Figure 7:
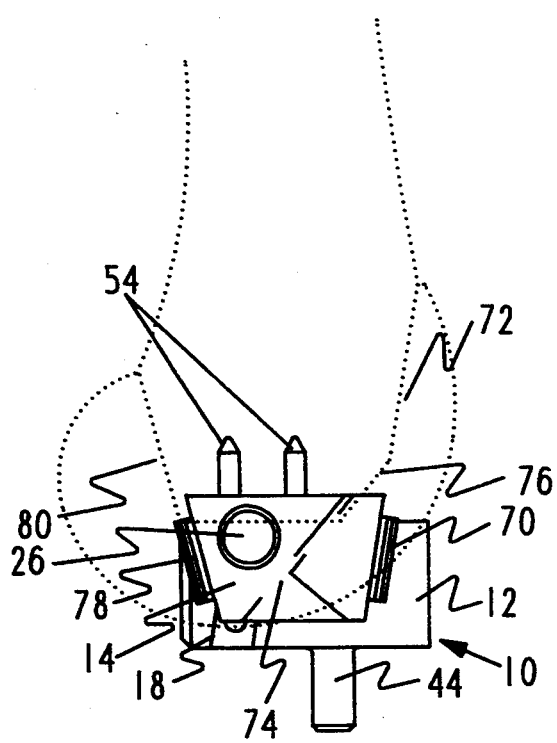
FIG. 7 is side plan view of selected components of the jig of FIG. 5 with the trial prosthesis shown in dotted outline.

I will now describe the operation of the jig 10 with reference to FIGS. 5 through 8. In FIGS. 5 through 8 the stem 40 is not shown. To use the jig 10, the surgeon exposes the distal femur and makes a planar resection on the end of the femur corresponding to surface 82 in FIG. 6. Other instruments are used to guide the surgeon in making this cut. For example, a suitable device has been distributed in the United States by Intermedics Orthopedics, Inc. in connection with the Natural-Knee ® System, mentioned above. A bore is established for the medullar shaft 40 using a separate instrument. Again, a suitable device has been distributed by Intermedics Orthopedics, Inc. in connection with the Natural-Knee ® System. The surface 82 on the medial condyle may be different from a surface 82' on the lateral condyle. For example, in FIG. 6, a trial prosthesis is shown with a plane surface 82 for the medial condyle and a separate plane surface 82' for the lateral condyle. In this situation, the jig 10 would be placed on the resected end of the femur as shown in plan view in FIG. 5. Orientation for a left or right knee is selected by manipulating the trial stem 40, as described above. The medial saw guide 14 is lower or more distal than the lateral saw guide 16. The medullar shaft 40 is inserted into the medullar canal and the saw guides are advanced against their respective resected planar surfaces. The bolts 26, 28 are tightened to further stabilize the saw guides 14, 16 during subsequent steps. For the medial condyle as shown in FIG. 7, passing a sagittal saw through the first anterior saw guide 70 produces the plane 72 against which the prosthesis or trial prosthesis will rest. A cut by the sagittal saw through second anterior slot 74 produces the surface 76. The slot 74 is shown in dashed outline in FIG. 7. Finally, a sagittal saw passed through the posterior slot 78 produces the surface 80 as shown in FIG. 7.

The attention of the surgeon would then be directed to the lateral condyle. As seen in FIG. 8, an incision with the sagittal saw through slot 70 produces the surface 72. Note that the surfaces 72 on both the medial and lateral condyle are co-planar. On the other hand, a cut through the second anterior slot 74 produces a plane 76' which is translated proximally and slightly anteriorly with respect to the surface 76 produced for the medial condyle and shown in FIG. 7. Finally, an incision through the posterior slot 78 produces the surface 80' along the posterior side of the femur. The surface 80' is also translated somewhat proximally and anteriorly with respect to the surface 80. Nevertheless, the planes 72, 76, 82 and 80 produce a similar and congruent geometry to the planes 72, 76', 82', and 80'. Thus, the same congruent geometry is maintained for each condyle. Shims, such as shim 86 shown in FIG. 6, may be inserted on the appropriate condyle, in this case the lateral condyle, to establish common contact with the condyles.

Use of this system permits the surgeon to retain as much of the patient's bone as possible, while compensating for the degeneration of the bone on either the medial or lateral condyle, depending circumstances.

My invention may be embodied in other specific forms without departing from the teachings thereof. The foregoing description is to be considered in all respects to be illustrative and not restrictive. The scope of my invention is defined by the following claims.

I claim as my invention:

1. A surgical jig for guiding a sagittal saw in connection with surgical preparation of a distal femur for receiving a femoral component of a knee prosthesis, said surgical jig comprising
    a central body adapted to generally fit in an intercondyle area of a distal end of a patient's femur, said central body having a proximal and a distal end,
    means, connected to said central body, for aligning said central body with the femur,
    at least one condyle saw guide, slidingly attached to said central body, and
    means for guiding said condyle saw guide on a path with respect to said central body which is displaced anteriorly from said proximal end to said distal end of said central body.

2. The surgical jig according to claim 1 wherein said saw guide comprises
    first slot means for controlling a sagittal saw blade to cut a first oblique anterior resected surface on said femur,
    second slot means for controlling a sagittal saw blade to cut a second oblique anterior resected surface on said femur, and
    third slot means for controlling a sagittal saw blade to cut a first oblique posterior resected surface on said femur.

3. The surgical jig according to claim 2 wherein said at least one saw guide comprises a medial saw guide and a lateral saw guide and said means for guiding said saw guide comprise a medial means for guiding said medial saw guide and a lateral means for guiding said lateral saw guide.

4. The surgical jig according to claim 3 wherein at least one of said means for guiding said saw guide comprise a dovetail tongue and mating groove.

5. The surgical jig according to claim 4 wherein both means for guiding said saw guides comprise a dovetail tongue and mating groove.

6. The surgical jig according to claim 5 wherein said means for guiding each further comprise a bolt for releasably securing a selected one of said saw guides in a selected location along said means for guiding.

7. The surgical jig according to claim 6 wherein said dovetail tongues are on said central body.

8. The surgical jig according to claim 7 wherein said means for aligning comprise a medullar stem.

9. The surgical jig according to claim 8 wherein said central body further comprises means for aligning said medullar stem for a patient's right or left femur.

10. The surgical jig according to claim 1 wherein said at least one saw guide comprises a medial saw guide and a lateral saw guide and said means for guiding said saw guide comprise a medial means for guiding said medial saw guide and a lateral means for guiding said lateral saw guide.

11. The surgical jig according to claim 10 wherein at least one of said means for guiding said saw guide comprise a dovetail tongue and mating groove.

12. The surgical jig according to claim 11 wherein both means for guiding said saw guides comprise a dovetail tongue and mating groove.

13. The surgical jig according to claim 12 wherein said means for guiding each further comprise a bolt for releasably securing a selected one of said saw guides in a selected location along said means for guiding.

14. The surgical jig according to claim 13 wherein said dovetail tongues are on said central body.

15. The surgical jig according to claim 14 wherein said means for aligning comprise an medullar stem.

16. The surgical jig according to claim 15 wherein said central body further comprises means for aligning said medullar stem for a patient's right or left femur.

* * * * *